(12) United States Patent
Drieu

(10) Patent No.: US 6,936,285 B1
(45) Date of Patent: Aug. 30, 2005

(54) **USE OF *GINKGO BILOBA* EXTRACTS FOR PREPARING A MEDICINE**

(75) Inventor: Katy Drieu, Paris (FR)

(73) Assignee: Societe de Conseils de Recherches d'Application Scientifiques (S.C.R.A.S. (FR)

( * ) Notice: Subject to any disclaimer, the term of this patent is extended or adjusted under 35 U.S.C. 154(b) by 0 days.

(21) Appl. No.: 09/555,906

(22) PCT Filed: Dec. 1, 1998

(86) PCT No.: PCT/FR98/02576

§ 371 (c)(1),
(2), (4) Date: Jun. 2, 2000

(87) PCT Pub. No.: WO99/27943

PCT Pub. Date: Jun. 10, 1999

(30) Foreign Application Priority Data

Dec. 3, 1997 (FR) .......................................... 97 15230

(51) Int. Cl.⁷ ...................... A61K 35/78; A61K 35/70
(52) U.S. Cl. .......................... 424/752; 424/725; 514/22
(58) Field of Search .............................. 424/195.1, 725, 424/752; 514/22

(56) References Cited

U.S. PATENT DOCUMENTS 5,541,183 A * 7/1996 Park et al. ............... 514/232.8

5,976,548 A * 11/1999 Hsia et al. ................ 424/195.1

FOREIGN PATENT DOCUMENTS

| EP | 04 31 535 | 6/1991 |
|---|---|---|
| EP | 04 31 536 | 6/1991 |
| EP | 04 36 129 | 7/1991 |
| JP | 0 52 71 083 | 10/1993 |

OTHER PUBLICATIONS

Remington's Pharmaceutical Sciences. Esol., A. et al. (eds.), Philadelphia College of Pharmacy and Science, pp. 1287–1296, 1980.*

Kleijnen, J. et al., *Ginkgo biloba*, Lancet, 340: 1136–1139, Nov. 1992.*

* cited by examiner

*Primary Examiner*—Christopher R. Tate
*Assistant Examiner*—Kailaash C. Srivastava
(74) *Attorney, Agent, or Firm*—Muserlian, Lucas and Mercanti

(57) ABSTRACT

The invention relates to the use of *Ginkgo biloba* extracts for preparing a medicament intended to ease the withdrawal of individuals dependent on the consumption of a substance engendering dependency and/or addiction, such as in particular alcohol, amphetamines, tobacco, drugs inducing toxicomania.

11 Claims, No Drawings

USE OF *GINKGO BILOBA* EXTRACTS FOR PREPARING A MEDICINE

This application is a 371 of PCT/FR98/02576 filed Dec. 1, 1998.

The invention relates to the use of extracts of *Ginkgo biloba* for preparing a medicament intended to ease the withdrawal of individuals who are dependent on the consumption of a substance engendering dependency and/or addiction such as in particular alcohol, amphetamines, tobacco and drugs inducing drug addiction.

It is already known that extracts of *Ginkgo biloba* have an activity in the cardiovascular field (in particular the reduction of platelet adhesion), in the central nervous field (in particular a neuroprotective activity) or in the neurosensory system (in particular retinal protection); cf. for example DeFeudis et al., *Ginkgo Biloba* Extract (EGb 761®), Pharmaceutical Activities and Clinical Applications (Elsevier, Paris, 1991). Their preparation has been the subject of a certain number of patents, of which there can be mentioned the European Patents EP 431 535 and EP 431 536, and the American Patent U.S. Pat. No. 5,389,370.

Now the Applicant has just found that certain extracts of *Ginkgo biloba* also have useful new pharmacological properties, namely easing the withdrawal of subjects addicted to alcohol or drugs, and more generally of subjects dependent on a substance engendering dependency and/or addiction. The Applicant observed that the administration of these extracts resulted in an attenuation of the withdrawal symptoms.

A subject of the invention is therefore the use of these extracts for preparing a medicament intended to ease the withdrawal of individuals dependent on the consumption of a substance engendering dependency and/or addiction, such as in particular alcohol, amphetamines, tobacco and drugs inducing drug addiction.

By drugs inducing toxicomania is understood in particular morphine and its derivatives, opium and opiates, cocaine, crack, and more generally all substances, including any medicamentous substances, on which a subject can become dependent.

By extract of *Ginkgo biloba* is understood at least one of the individual compounds which can be obtained by extraction from the *Ginkgo biloba L* tree, and in particular a flavonoid compound or a terpene such as a ginkgolide or a bilobalide, or also a mixture of the latter. Preferably, the extract used will be such that it contains an effective quantity of ginkgolides. For the uses according to the invention, an extract of type EGb 761 or CP 401 can for example be chosen.

By ginkgolide is understood all the natural ginkgolides obtained from the *Ginkgo biloba* tree, as well as synthetic ginkgolides and their derivatives (resulting for example from an acetylation or alkoxylation reaction) and pharmaceutically active salts. The ginkgolides used can for example be ginkgolide A, ginkgolide B, ginkgolide C, ginkgolide J or ginkgolide M (structures given in the diagram below; these compounds can be isolated from extracts of *Ginkgo biloba* leaves—see *GINKGOLIDES, Chemistry, Biology Pharmacology and Clinical Perspectives*, published by P. Braquet, J. R. Prous Science Publishers, in particular Volumes 1 (1988) and 2 (1989)). Glycosylated derivatives of ginkgolides or alkoxylated or acetylated derivatives of ginkgolides can also be used. By alkoxylated derivative of ginkgolide is understood a ginkgolide derivative comprising at least one linear or branched alkoxy group, instead of a hydroxy group (these compounds are described in French Patent Application No. FR 88.14392). Similarly, by acetylated derivative of ginkgolide is understood a derivative of ginkgolide comprising at least one acetate group instead of a hydroxy group.

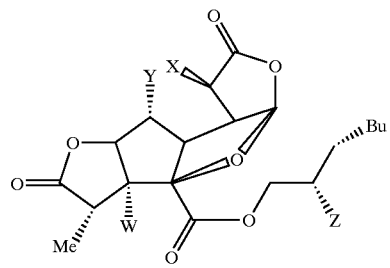

Structure of ginkgolides A, B, C, J and M

| Ginkgolide | W  | X  | Y  | Z  |
|------------|----|----|----|----|
| A          | OH | OH | H  | H  |
| B          | OH | OH | OH | H  |
| C          | OH | OH | OH | OH |
| J          | OH | OH | H  | OH |
| M          | H  | OH | OH | OH |

By extract of type EGb 761 is understood an extract of a composition substantially identical to that of the standardized extract EGb 761 as defined in particular in the following article: K. Drieu, La presse medicale, 31, 25 Sept. 1986, supplement devoted to the extract of *Ginkgo biloba* (EGb 761), 1455–1457; or in the European Patents EP 431 535 and EP 431 536; by extract of type EGb 761 is therefore understood in particular extracts of *Ginkgo biloba* comprising 20 to 30% of flavoneglycosides, 2.5 to 4.5% of ginkgolides A, B, C and J, 2 to 4% of bilobalide, less than 10% of proanthocyanidines and less than 10 ppm, and preferably less than 5 ppm, of compounds of alkylphenol type, and in particular extracts of *Ginkgo biloba* comprising approximately 24% of flavoneglycosides, 3.1% of ginkgolides A, B, C and J, 2.9% of bilobalide, 6.5% of proanthocyanidines and less than 1 ppm of compounds of alkylphenol type. By extract of type CP 401 is understood extracts such as those which are presented in the U.S. Pat. No. 5,389,370, in particular extracts of *Ginkgo biloba* containing 5.5 to 8% of ginkgolides A, B, C and J, 40 to 60% of flavoneglycosides and 5 to 7% of bilobalide, and quite particularly extracts containing approximately 7% of ginkgolides A, B, C and J, 50% of flavoneglycosides and 6% of bilobalide.

According to another aspect of the invention, the extract of *Ginkgo biloba* used will comprise more than 5% of ginkgolides, and more preferably more than 50% of ginkgolides.

The invention also relates to the use of a ginkgolide or one of its derivatives or pharmaceutically active salts for preparing a medicament intended to ease the withdrawal of individuals dependent on the consumption of a substance engendering dependency and/or addiction, such as in particular alcohol, amphetamines, tobacco and drugs inducing drug addiction. Preferably, the ginkgolide used for this aspect of the invention will be ginkgolide A or ginkgolide B.

The invention also relates to the use of a compound of general formula (I)

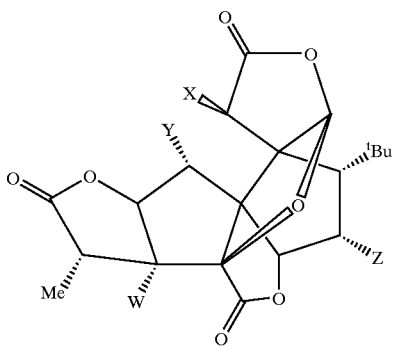

(I)

in which W, X, Y and Z independently represent the H, OH, linear or branched alkoxy or O—$G_s$, $G_s$—OH radicals representing a mono- or disaccharide, or one of their derivatives or analogues, it being understood that at least one of W, X, Y or Z represents an O—$G_s$ radical, for preparing a medicament intended to ease the withdrawal of individuals dependent on the consumption of a substance engendering dependency and/or addiction, such as in particular alcohol, tobacco, amphetamines, drugs inducing drug addiction.

The invention preferably relates to the use of a compound of general formula (I)

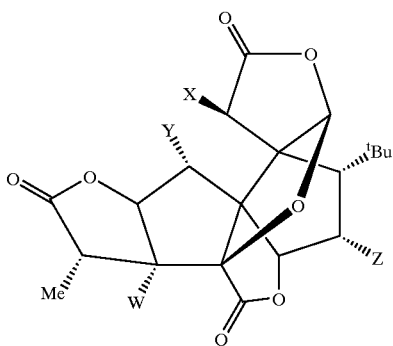

(I)

in which X represents an Oh or O—$G_s$ radical, $G_s$—OH representing a mono- or disaccharide, or one of their derivatives or analogues, and:
  either W represents an OH or O—$G_s$—OH radical, Y represents H and Z represents H;
  or W represents an OH or O—$G_s$ radical, Y represents an OH or O—$G_s$ radical and Z represents H;
  or W represents an OH or O—$G_s$ radical, Y represents an OH or O—$G_s$ radical and Z represents and OH or O—$G_s$ radical;
  or W represents an OH or O—$G_s$ radical, Y represents an H and Z represents an OH or O—$G_s$ radical;
  or W represents H, Y represents and OH or O—$G_s$ radical and Z represents an OH or O—$G_s$ radical;
  or W represents an OH or O—$G_s$ radical, Y represents a linear or branched alkoxy radical and Z represents H;
  it being understood that at least one of W, X, Y or Z represents an O—$G_s$ radical,
  for preparing a medicament intended to ease the withdrawal of individuals dependent on the consumption of a substance engendering dependency and/or addiction, such as in particular alcohol, tobacco, amphetamines drugs inducing drug addiction.

The invention relates quite particularly to the use of a compound of general formula (I)

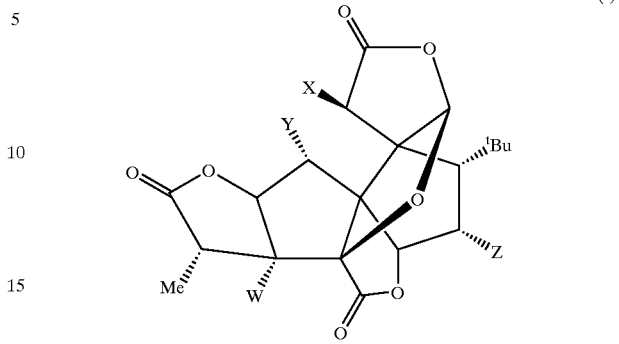

(I)

in which X represents an OH or O—Gs radical, Gs—OH representing a mono- or disaccharide, or one of their derivatives or analogues, and:
  either W represents an OH or O—Gs radical, Y represents H and Z represents H;
  or W represents an OH or O—Gs radical, Y represents an OH or O—Gs radical and Z represents H;
  or W represents an OH or O—$G_s$ radical, Y represents a linear or branched alkoxy radical and Z represents H;
  it being understood that at least one of W, X, Y or Z represents an O—$G_s$ radical, for preparing a medicament intended to ease the withdrawal of individuals dependent on the consumption of a substance engendering dependency and/or addiction, such as in particular alcohol, tobacco, amphetamines drugs inducing drug addiction.

By linear or branched alkoxy radical is understood in the present description an alkoxy radical the linear or branched carbon containing chain of which contains 1 to 6 carbon atoms. By derivative or analogue of mono- or disaccharides is understood compounds such as N-acetylglucosamine, N-acetylalosamine, galactosamine, mannoseamine, N-tosylhydrazone, etc.

Preferably, O—$G_s$ will be chosen such that $G_s$—OH belongs to the group comprising abequose, rhamnose, arabinose, ribose, xylose, 2-deoxy-ribose, glucose, galactose, mannose, 2-deoxyglucose, fructose, fucose, N-acetylglucosamine, N-acetylalosamine, galactosamine, mannosamine, saccharose, lactose, maltose, cellobiose and trehalose. Even more preferentially, O—$G_s$ will be chosen such that $G_s$—OH belongs to the group comprising glucose and lactose.

The invention therefore also relates to the use of glycosylated derivatives of ginkgolides, more particularly those of ginkgolides A and B, the glycosyl groups suitable for the invention having been described previously.

The different processes for obtaining glycosylated derivatives of ginkgolides or alkoxylated ginkgolides (i.e. those resulting from a glycosylation reaction carried out on at least one of the OH groups of ginkgolides or their alkoxylated derivatives) are described in the following publication: Weber, M. and Vasella, A., Helv. Chim. Acta, 80 (1997), 2352–2367.

The pharmaceutical compositions comprising a compound of the invention can be in the form of solids, for example powders, granules, tablets, gelatin capsules, liposomes or suppositories. Appropriate solid supports can be, for example; calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, as well as their mixtures, in varying proportions, in water.

The administration of a medicament according to the invention can be carried out by topical, oral, parenteral route, by injection (intramuscular, sub-cutaneous, intravenous, etc.), etc.

The administration dose envisaged for a medicament according to the invention is comprised between 0.1 mg and 10 g according to the type of substance on which the subject to be treated is dependent.

Unless they are defined differently, all the technical and scientific terms used here have the same meaning as that usually understood by an ordinary specialist in the field to which this invention belongs. Similarly, all publications, patent applications, all patents and all other references mentioned here are incorporated by way of reference.

PHARMACOLOGICAL STUDY OF THE PRODUCTS OF THE INVENTION

1. Study of the Effects of Extracts of Ginkgo Biloba on Alcohol Dependency

Two studies were carried out: one relates to the effects of EGb 761, the other to the effects of another extract of Ginkgo biloba, CP 401, which does not contain bilobalide but twice as much ginkgolides as EGb 761(6%).

1) Rats are treated for 15 days with alcohol (they are administered 10% ethanol in their drinking water for the first week and then 12.5% ethanol). They are given 50 or 100 mg/kg of EGb 761 per day by oral route (gavage) for the 5 days before the absorption of alcohol is stopped (from the 11th day) and the 3 days after it is stopped.

The behavioural symptoms were evaluated for 3 days after the absorption of alcohol is stopped in three groups of rats (n=6): the control group having received only alcohol, one group having received alcohol and treatment with 50 mg/kg of EGb 761 and another group having received alcohol and treatment with 100 mg/kg of EGb 761, the treatments with EGb 761 having been administered under the conditions described above. The results of these tests are shown in table (I) which can be found in appendix I.

In the animals which received EGb 761, it can be observed that the withdrawal symptoms (7 criteria) are reduced in a dose-dependent manner and that the animals also have reduced motor hyperactivity.

2) Rats are treated for 15 days with alcohol (they are given 10% ethanol in their drinking water for the first week and then 12.5% ethanol). They are administered 50 mg/kg of CP 401 extract per day by oral route (gavage) for the 5 days before the absorption of alcohol is stopped (from the 11th day) and the 3 days after it is stopped.

The behavioural symptoms were evaluated for the 3 days after the absorption of alcohol was stopped in three groups of rats (n=6): the control group only having received alcohol and the other group having received alcohol and treatment with 50 mg/kg of CP 401 extract administered under the conditions described above. The results of these tests are shown in table (II) which can be found in appendix I.

It is observed that the animals which received the CP 401 extract show a reduction in the symptoms linked with withdrawal compared with the intoxicated control animals.

2. Study of the Effects of Ginkgo Biloba Extracts on Sensitization to Amphetamine An injection of amphetamine (0.5 mg/kg IP) provokes motor hyperactivity in the rat (measured by actimetry). Administration eight times, every other day, of the same dose of amphetamine results in a progressive increase in locomotive activity: this phenomenon is called "sensitization".

For 8 days before the administration of amphetamine and throughout this administration, rats (n=8) subjected to the administration of amphetamine as described above were subjected to treatment by oral route with a dose of EGb 761 of 100 mg/kg per day or of a dose of 5 mg/kg per day of ginkgolide A.

Actimetry measurements were carried out for 1 hour after the administration of the amphetamine on the 9th (first day on which amphetamine was administered), 13th, 17th, 21st and 25th day. The results of these tests are shown in A which can be found in appendix II.

It is observed that behavioural sensitization to amphetamine is reduced in the animals which received 5 mg/kg per day of ginkgolide A. An enhanced and quite significant effect is observed with EGb 761 at 100 mg/kg per day.

3. Study of the Effects of Ginkgo Biloba Extract EGb 761 on Morphine Withdrawal Syndrome Rats are treated every 8 hours (3 times per day) for 10 days with a dose of morphine by sub-cutaneous route resulting in motor hyperactivity (measured by actimetry). On the 11th day, they are administered naloxone (3 mg/kg IP) and the withdrawal signs are observed for 60 minutes: a series of behavioural signs is quantified, a series measured (hypothermia, weight loss) or a series graded (scale with 4 levels).

Two groups of 8 rats are treated with EGb 761 (50 or 100 mg/kg per day) for 4 days before the administration of naloxone and 2 hours before it. A group of intoxicated control rats only receives injections of morphine before the naloxone and an absolute control group only receives naloxone.

Statistical analysis of the batches is carried out using the following tests: parametric Anova, Barlett's test to check the homogeneity of variances and Dunnett's test for multiple comparisons.

The results quantified by counting for the different behavioural parameters analyzed are shown in table (III) which can be found in appendix III.

APPENDIX I

TABLE I

Influence of treatment with substance EGb 761 on the number of observations of each symptom of abstinence at 24 hours after withdrawal

| Treatment (mg/kg) | TRE | SNO | CHA | TWI | MOT | ESC | JUM |
|---|---|---|---|---|---|---|---|
| none | 3 | 7 | 6 | 5 | 6 | 6 | 6 |
| EGb 761 (50) | 3 | 5 | 3 | 2 | 2 | 3 | 2 |
| EGb 761 (100) | 0 | 2 | 2 | 1 | 2 | 0 | 1 |

TABLE II

Influence of treatment with substance CP 401 on the number of observations of each symptom of abstinence at 24 hours after withdrawal

| Treatment (mg/kg) | TRE | SNO | CHA | TWI | MOT | ESC | JUM |
|---|---|---|---|---|---|---|---|
| none | 3 | 8 | 6 | 7 | 4 | 6 | 6 |
| CP 401 (50) | 2 | 6 | 3 | 3 | 1 | 4 | 3 |

| Legend common to Tables I and II | |
|---|---|
| TRE: | trembling in body |
| SNO: | snorting |
| CHA: | chattering of teeth |
| TWI: | twitching of ears |
| MOT: | motor activity |
| ESC: | attempted escapes |
| JUM: | jumps |

The symptoms are graded from 0 to 3 according to their intensity (0 = slight; 3 = very pronounced).

APPENDIX III

TABLE III

Influence of treatment with substance EGb 761 on the number of observations of each of the symptoms of abstinence during morphine withdrawal

| Symptoms | Group 1 | Group 2 | Group 3 |
|---|---|---|---|
| Jumps | 0.0 ± 0.0 | 1.00 ± 0.33 | 0.50 ± 0.19 |
| Stiffening | 9.88 ± 1.03 | 1.13 ± 0.40 | 5.63 ± 1.00 |
| Snorting | 0.25 ± 0.16 | 2.75 ± 0.70 | 0.88 ± 0.29 |
| Jerking of head | 0.0 ± 0.0 | 5.50 ± 1.13 | 2.43 ± 0.48 |
| Yawning | 0.75 ± 0.41 | 2.00 ± 0.78 | 0.88 ± 0.40 |
| Chattering or grinding of teeth | 0.0 ± 0.0 | 4.75 ± 0.86 | 1.75 ± 0.45 |
| Burying | 0.25 ± 0.16 | 1.38 ± 0.46 | 0.25 ± 0.16 |
| Excessive scratching | 0.0 ± 0.0 | 1.13 ± 0.48 | 0.38 ± 0.26 |
| Grooming | 6.00 ± 1.39 | 1.38 ± 0.53 | 4.25 ± 1.31 |

Legend
  Group 1: control;
  Group 2: group treated only with morphine (3 times 10 mg/kg/day);
  Group 3: group treated with morphine and with EGb 761 at a dose of 100 mg/kg.

What is claimed is:

1. A method of alleviating withdrawal symptoms of dependency or addiction to a substance selected from the group consisting of alcohol, amphetamines and morphine in a human being comprising administering to said human being in need thereof a *Ginkgo biloba* extract in an amount sufficient to alleviate said withdrawal symptoms, wherein said *Ginkgo biloba extract* comprises 20 to 30% of flavoneglycosides, 2.5 to 4.5% of ginkgolides A, B, C and J, 2 to 4% of bilobalide, less than 10% of proanthocyanidines and less than 10 ppm of compounds of alkylphenol type.

2. The method of claim 1 wherein the *Ginkgo biloba* extract comprises less than 5 ppm of compounds of alkylphenol type.

3. The method of claim 1 wherein the withdrawal symptoms are selected from the group consisting of trembling in body, chattering of teeth and decreased motor activity.

4. The method of claim 3 wherein the withdrawal symptoms is trembling in body.

5. The method of claim 3 wherein the withdrawal symptom is chattering of teeth.

6. The method of claim 3 wherein the withdrawal symptom is decreased motor activity.

7. A method of alleviating withdrawal symptoms of dependency or addiction to a substance selected from the group consisting of alcohol, amphetamines and morphine in a human being comprising administering to said human being in need thereof a *Ginkgo biloba* extract in an amount sufficient to alleviate said withdrawal symptoms, wherein said *Ginkgo biloba* extract comprises 5.5 to 8% of ginkgolides A, B, C and J, 40 to 60% of flavonglycosides and 5 to 7% of bilobalide.

8. The method of claim 7 wherein the withdrawal symptoms are selected from the group consisting of trembling in body, chattering of teeth and decreased motor activity.

9. The method of claim 8 wherein the withdrawal symptom is trembling body.

10. The method of claim 8 wherein the withdrawal symptom is chattering of teeth.

11. The method of claim 8 wherein the withdrawal symptom is decreased motor activity.

* * * * *